(12) United States Patent
Sanders

(10) Patent No.: US 7,957,005 B2
(45) Date of Patent: *Jun. 7, 2011

(54) FIBER OPTIC APPARATUS AND METHOD FOR SENSING HAZARDOUS MATERIALS

(75) Inventor: Glen A. Sanders, Scottsdale, AZ (US)

(73) Assignee: Honeywell International Inc., Morristown, NJ (US)

( * ) Notice: Subject to any disclaimer, the term of this patent is extended or adjusted under 35 U.S.C. 154(b) by 1162 days.

This patent is subject to a terminal disclaimer.

(21) Appl. No.: 11/831,525

(22) Filed: Jul. 31, 2007

(65) Prior Publication Data

US 2010/0027023 A1  Feb. 4, 2010

(51) Int. Cl.
*G01B 9/02* (2006.01)
(52) U.S. Cl. .......................................... 356/483
(58) Field of Classification Search .................. 356/480, 356/478, 481, 517, 451; 385/12, 13; 250/227.14–227.18, 227.23; 422/82.25, 422/82.11

See application file for complete search history.

(56) References Cited

U.S. PATENT DOCUMENTS

| | | | |
|---|---|---|---|
| 6,778,279 B2 * | 8/2004 | Lange et al. | 356/483 |
| 7,382,945 B1 * | 6/2008 | Sanders | 385/12 |
| 7,388,671 B2 * | 6/2008 | Sanders et al. | 356/461 |
| 7,483,144 B2 * | 1/2009 | Sanders | 356/480 |
| 7,518,730 B2 * | 4/2009 | Yates et al. | 356/480 |
| 7,796,262 B1 * | 9/2010 | Wang et al. | 356/436 |

* cited by examiner

*Primary Examiner* — Hwa S. A Lee
(74) *Attorney, Agent, or Firm* — Fogg & Powers LLC

(57) ABSTRACT

An apparatus and method for sensing hazardous materials utilizes first and second optical fibers and a recirculator coupled to a substrate. The first optical fiber is coupled to the substrate and has first and second opposing ends and a first substance embedded therein. The first substance is reactive to a first hazardous material type. The second optical fiber is coupled to the substrate and has first and second opposing ends and a second substance embedded therein. The second substance is reactive to a second hazardous material type. The at least one recirculator is coupled to the substrate and configured such that when light propagates from one of the ends of at least one of the first and second optical fibers, at least some of the light is directed by the at least one recirculator into the opposing end of the respective optical fiber.

19 Claims, 9 Drawing Sheets

FIBER OPTIC APPARATUS AND METHOD FOR SENSING HAZARDOUS MATERIALS

TECHNICAL FIELD

The present invention generally relates to environment sensing, and more particularly relates to optical-based systems and methods for detecting the presence of a specific material.

BACKGROUND

In recent years, greater emphasis has been placed on national homeland security, including the detection of various threats to human populations. In particular, detecting or sensing the presence of undesirable hazardous materials in the environment, such as biological or chemical agents and sources of radioactivity, has become a priority. Such hazardous materials may be found in shipping containers, buildings, airports, or other locations and may be directed at inflicting civilian, as well as military, casualties. As such, there is a need to provide small, affordable devices that are capable of accurately detecting a wide range of hazardous materials.

Accordingly, it is desirable to provide a sensor capable of sensing biological, chemical, and/or radioactive hazardous materials. In addition, it is desirable to provide a sensor for detecting the presence of multiple and different threats while minimizing the package size and manufacturing costs of the sensor. Furthermore, other desirable features and characteristics of the present invention will become apparent from the subsequent detailed description of the invention and the appended claims, taken in conjunction with the accompanying drawings and this background of the invention.

BRIEF SUMMARY

In one embodiment, an apparatus for sensing hazardous materials is provided. The apparatus includes a substrate, first and second optical fibers, and at least one recirculator. The first optical fiber is coupled to the substrate and has first and second opposing ends and a first substance embedded therein. The first substance is reactive to a first hazardous material type. The second optical fiber is coupled to the substrate and has first and second opposing ends and a second substance embedded therein. The second substance is reactive to a second hazardous material type. The at least one recirculator is coupled to the substrate and configured such that when light propagates from one of the ends of at least one of the first and second optical fibers, at least some of the light is directed by the at least one recirculator into the opposing end of the respective optical fiber.

In another embodiment, a fiber optic hazardous material sensor is provided. The fiber optic hazardous material sensor includes a substrate, a tunable light source, a first plurality of optical fibers, a second plurality of optical fibers, at least one recirculator, and a multiplexer. The tunable light source is on the substrate and operable to emit light. The first plurality of optical fibers is coupled to the substrate and each has first and second opposing ends and a respective first substance therein. The first substances are each reactive to a first hazardous material type. The second plurality of optical fibers is coupled to the substrate and each has first and second opposing ends and a respective second substance therein. The second substances are each reactive to a second hazardous material type. The at least one recirculator is on the substrate and configured such that a portion of the light emitted by the tunable light source is transmitted therethrough and when light propagates from one of the ends of at least one of the optical fibers, at least some of the light is directed by the at least one recirculator into the opposing end of the respective optical fiber. The multiplexer is on the substrate and coupled between the tunable light source and the first and second plurality of optical fibers. The multiplexer is configured to selectively direct the light from the tunable light source to at least one of the optical fibers of the first and second pluralities of optical fibers. The at least one recirculator and the at least one of the optical fibers jointly form a resonator having a resonance frequency.

In a further embodiment, a method for sensing hazardous materials is provided. Light is generated with a tunable light source. At least one recirculator and first and second optical fibers having first and second opposing ends and respective first and second substances embedded therein are arranged such that a beam of the light generated with the tunable light source is transmitted by the at least one recirculator, enters the first end of a selected one of the first and second optical fibers, and is emitted from the second end of the selected optical fiber onto the at least one recirculator. A first portion of the beam of light is reflected by the at least one recirculator into the first end of the selected optical fiber and a second portion of the beam of light is transmitted by the at least one recirculator such that the at least one recirculator and the selected one of the first and second optical fibers jointly form a resonator having a resonance frequency. The first substance is reactive to a first hazardous material type and the second substance is reactive to a second hazardous material type such that the resonator has a first round-trip loss value during an absence of the respective hazardous material type and a second round-trip loss value during a presence of the respective hazardous material type. The second portion of the beam of light transmitted by the at least one recirculator is captured to determine a present round-trip loss value for the resonator. The tunable light source is tuned through the resonance of the resonator to determine present resonance properties of the resonance line shape. The present resonance properties are monitored. A change in the resonance properties is indicative of a change in the round-trip loss value and the presence of the respective hazardous material type.

In a further embodiment, a method for sensing hazardous materials is provided. Light is generated with a tunable light source. At least one recirculator and first and second optical fibers having first and second opposing ends and respective first and second substances embedded therein are arranged such that a beam of the light generated with the tunable light source is transmitted by the at least one recirculator, enters the first end of a selected one of the first and second optical fibers, and is emitted from the second end of the selected optical fiber onto the at least one recirculator. A first portion of the beam of light is reflected by the at least one recirculator into the first end of the selected optical fiber, and a second portion of the beam of light being transmitted by the at least one recirculator such that the at least one recirculator and the selected one of the first and second optical fibers jointly form a resonator having a resonance frequency. The first substance is reactive to a first hazardous material type and the second substance is reactive to a second hazardous material type such that the resonator has a first round-trip loss value during an absence of the respective hazardous material type and a second transmission value at the during a presence of the respective hazardous material type. The second portion of the beam of light is transmitted by the at least one recirculator to determine a present round-trip loss value for the resonator. The tunable light source is tuned through the resonance of the resonator to determine present resonance properties of the resonance line shape. The present resonance properties are monitored. A change in the resonance properties is indicative of a change in the round-trip loss value and the presence of the respective hazardous material type.

In yet a further embodiment, an apparatus for sensing hazardous materials is provided. The apparatus includes a substrate, at least two coils of optical fiber, each of which has first and second reflective endfaces to form at linear resonator within each coil. The first optical fiber is coupled to the substrate and has first and second opposing ends and a first substance embedded therein. The first substance is reactive to a first hazardous material type. The second optical fiber is coupled to the substrate and has first and second opposing ends and a second substance embedded therein. The second substance is reactive to a second hazardous material type. Each of the reflective endfaces is coupled to the substrate, and each first reflective endface is configured to receive light propagating from within or on top of the substrate. The reflective endfaces of the each fiber coil are configured such that resonance light propagates back and forth within the fiber coil, forming a linear resonator. Each of the second endfaces is configured to transmit a portion of light to a photo-detector on the substrate. Variations of this embodiment exist, and in particular, variations exist in which more than one such second endface transmits light to the same photo-detector.

In yet a further embodiment, an apparatus for sensing hazardous materials is provided. The apparatus includes a substrate, at least two coils of optical fiber, each of which is coupled to two ports of a 4-port fiber optic coupler to form a ring resonator. Each fiber optic coupler is also coupled to the substrate via its two other ports. The coil of optical fiber has a first substance embedded therein. The first substance is reactive to a first hazardous material type. The second optical fiber has a second substance embedded therein. The second substance is reactive to a second hazardous material type. Each of the fiber optic couplers is coupled to the substrate to receive light propagating from within or on top of the substrate. Each coupler and fiber coil is configured such that resonance light propagates multiple times around the fiber coil, forming a ring resonator. Each of the couplers is configured to transmit a portion of light to a photo-detector on the substrate. Variations of this embodiment exist, and in particular, variations exist in which more than one such second endface transmits light to the same photo-detector.

BRIEF DESCRIPTION OF THE DRAWINGS

The present invention will hereinafter be described in conjunction with the following drawing figures, wherein like numerals denote like elements.

DETAILED DESCRIPTION

The following detailed description of the invention is merely exemplary in nature and is not intended to limit the invention or the application and uses of the invention. Furthermore, there is no intention to be bound by any theory presented in the preceding background of the invention or the following detailed description of the invention. It should also be noted that FIGS. 1-10 are merely illustrative and may not be drawn to scale.

An apparatus and method are provided for sensing one or more hazardous materials (i.e., biological or chemical agents and/or radiation types) in an environment. In general, the apparatus comprises a first optical fiber embedded with a first substance that reacts to a predetermined biological or chemical agent, a second optical fiber embedded with a second substance that reacts to a predetermined radiation type, and a recirculator that jointly forms at least one resonator with the first and second optical fibers. When an input light beam (e.g., from a light source) is supplied to the resonator and the input light beam is tuned to the resonance frequency of the resonator, a resonance lineshape is produced in the region of the resonance frequency, which is sensed by the light circulating through the resonator.

In the absence of the hazardous materials to be detected, the resonance lineshape has a narrow profile (i.e., or a high "finesse") corresponding to a low energy loss of the light circulating in the resonator (i.e., a first or low round-trip loss value of the resonator). When the optical fibers are exposed to one of the predetermined optical fibers, the first or second substance reacts thus altering the optical characteristics of the respective optical fiber. As a result, a portion of the light circulating in the optical fiber coil is scattered or absorbed. The normally narrow, resonance lineshape changes to a wider, shallower profile (i.e., or a low finesse). This change in resonance lineshape represents a greater energy loss resulting from the scattered light or absorbed light (i.e., a second or high round-trip loss value of the resonator) and thus, indicates the presence of one of the predetermined hazardous materials. Multiple optical fiber coils may be networked or multiplexed (e.g. time division multiplexed) together in the sensor to form multiple resonators for simultaneous detection of the presence of multiple hazardous materials.

Figure 1:
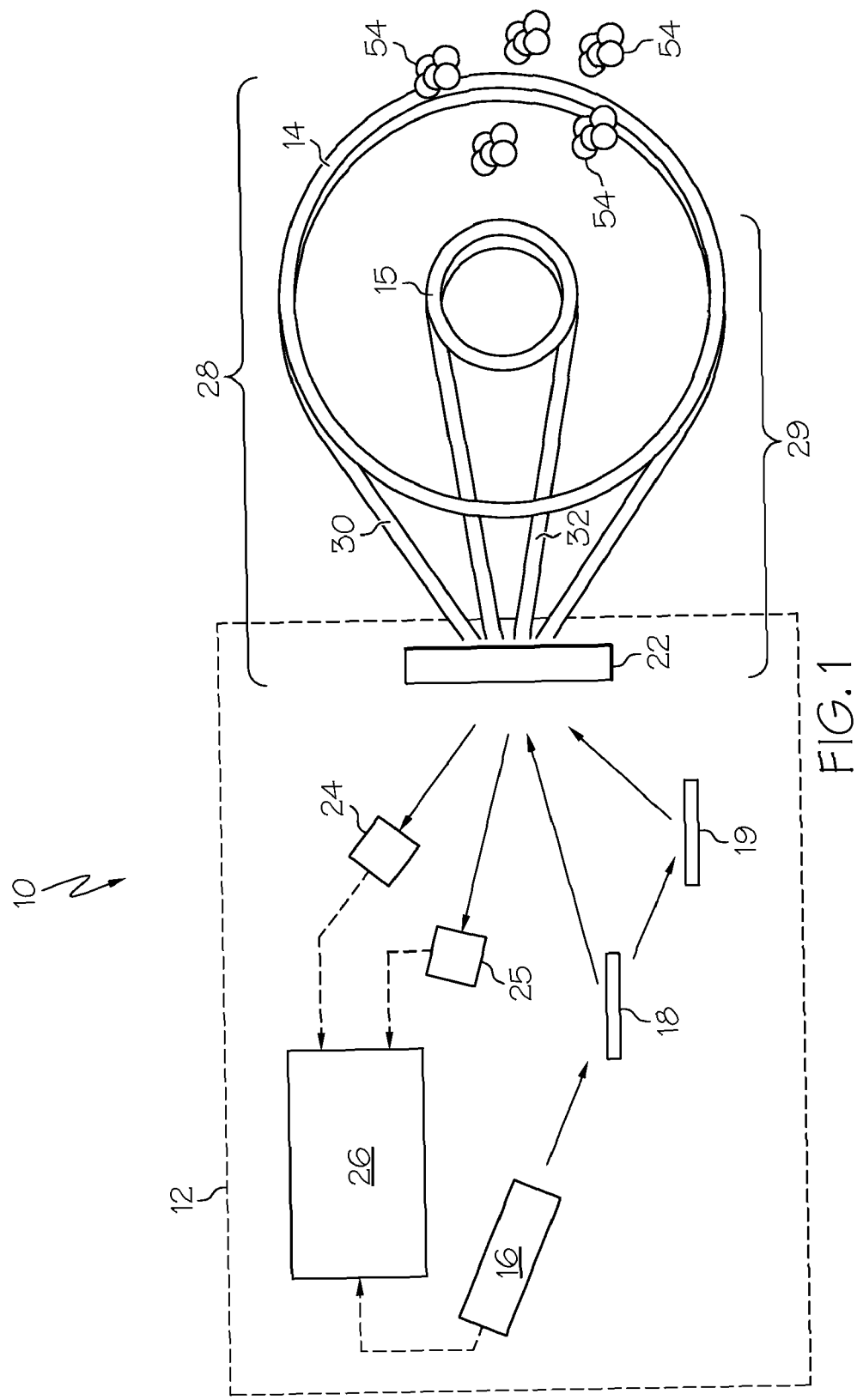
FIG. 1 is a schematic diagram of a hazardous material sensor in accordance with an exemplary embodiment of the present invention.

Referring now to the drawings, FIG. 1 schematically illustrates a hazardous material sensor 10 in accordance with an exemplary embodiment of the present invention. The sensor 10 comprises an integrated optical chip (IOC) 12 and optical fibers (or fiber optic cables) 14 and 15. In one embodiment, the IOC 12 includes a tunable light source 16 (e.g., a laser diode), a first reflector with partial transmittance 18, a second reflector 19, a recirculator 22 (e.g., a highly reflective mirror with low, but non-zero transmittance), photo-detectors (e.g., photodiodes) 24 and 25, and electronic circuitry 26 coupled to photo-detectors 24 and 25 and the light source 16. The recirculator 22 and the optical fibers 14 and 15 jointly form two resonators 28 and 29 respectively (although more could be adding by similar means). The resonators 28 and 29 may have a variety of configurations, and some exemplary embodiments are described herein. In one embodiment, the light introduced to the resonators 28 and 29 is monochromatic and circulates through multiple turns of the optical fibers 14 and 15, respectively, and for multiple passes through each coil using the recirculator 22.

In an exemplary embodiment, the light source 16 is a tunable laser having frequency stability, substantially narrow line width, and relatively high power capability. The light source 16 is tuned through a frequency region containing a frequency $f_0$ that corresponds with a resonance frequency in either the clockwise (CW) or counter-clockwise (CCW) direction of light propagation through each optical fiber resonator. In general, the recirculator 22 may be any optical element that reintroduces light emerging from one end of the optical fiber coil into the other end of the fiber coil, thus causing light to propagate through the optical fiber coil many times. The use of an input mirror instead of a fiber optic coupler for the recirculator 22 is one advantage of the sensor 10 since the mirror may be used to attenuate polarization errors and other error mechanisms, and may introduce fewer imperfections.

Figure 2:
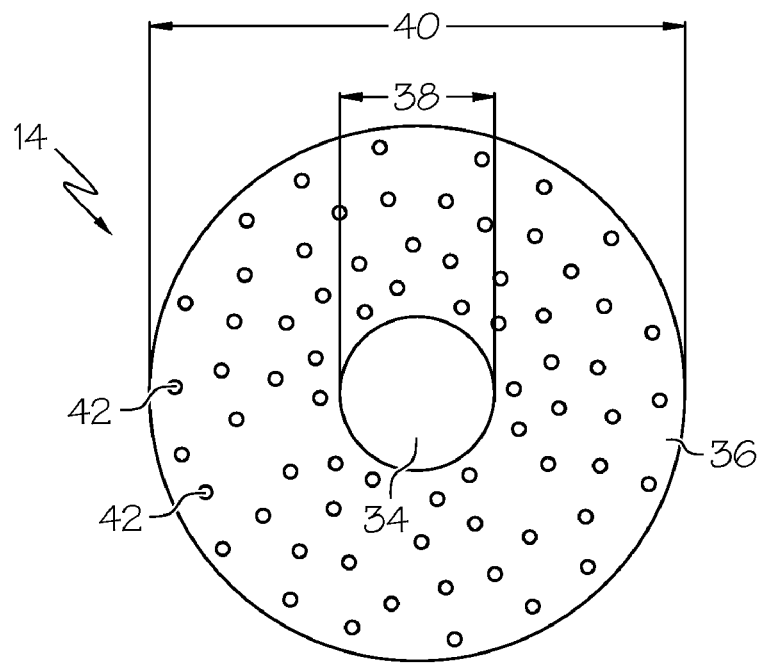
FIG. 2 is a cross-sectional view of a first optical fiber within the hazardous material sensor of FIG. 1.

The optical fibers 14 and 15 include at least first and second optical fiber ends 30 and 32, respectively, and each of the optical fibers 14 and 15 is wound into a coil. FIG. 2 illustrates a cross-section of the first optical fiber 14. As shown, the first optical fiber 14 is substantially circular and includes a core 34 and a cladding 36. In one embodiment, the core 34 is made of silica glass with an index of refraction (n) of approximately 1.47 and has a diameter 38 of, for example, between 5 and 10 micrometers (μm). The cladding 36 may be made of a permeable material with an index of refraction less than 1.47 (e.g., between 1.3 and 1.4) and have a biological or chemical indicator (or first substance) 42 embedded therein. In one embodiment, the cladding 36 is made of an acrylate polymer and has a diameter 40 of between 100 and 150 μm. The biological or chemical indicator 42 may be a chemical or other substance that reacts to one or more biological or chemical substances or materials, such as a biological agent or chemical compound, (e.g., hydrogen sulfide, cyanide, chlorine, nerve agents, serin, and the like) and changes optical characteristics, for example color, optical loss, index of refraction, or the like, when exposed to such biological or chemical substances or materials.

As will be appreciated by one skilled in the art, the indicator 42 may be embedded within the cladding 36 during the formation thereof. The fiber architecture shown in FIG. 2 is intended to guide a single spatial mode of light within core, which is very advantageous for high making high sensitivity resonators. However, thin silica core with a polymer may present physical strength deficiencies. As such, core 34 may be replaced by a two-concentric-layer glass structure (not shown) with an air-hole pattern using micro-structured fibers to enlarge the core and mode size of the light, and therefore remain single mode yet have a larger glass diameter for the core 34. Glass sizes of up to 30-50 microns may be realized, which are physically much stronger.

Figure 3:
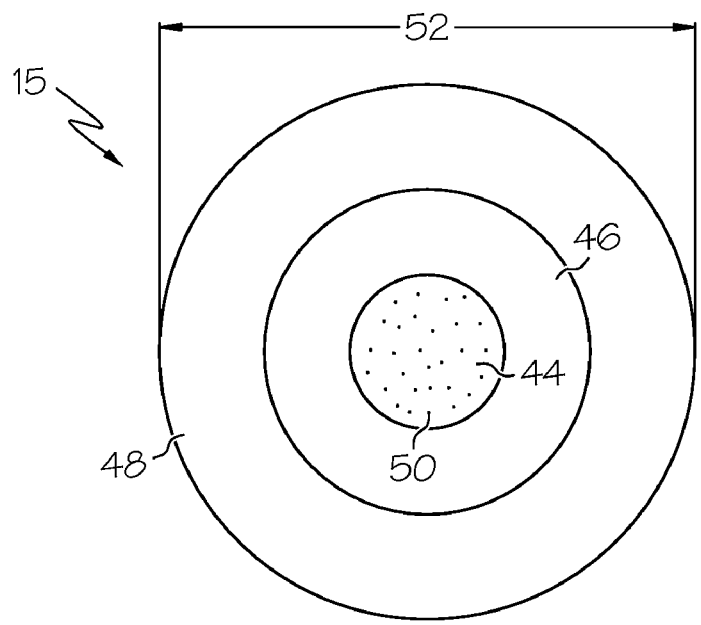
FIG. 3 is a cross-sectional view of a second optical fiber within the hazardous material sensor of FIG. 2.

FIG. 3 illustrates a cross-section of the second optical fiber 15. The second optical fiber 15 includes a core 44, a cladding 46, and a jacket 48. The core 44 may be similar to the core 34 of the first optical fiber 30 shown in FIG. 2. However, the core 44 of the second optical fiber 15 may be doped with a radio-actively-sensitive dopant (or second substance) 50, such as phosphorous (P) or boron (B), which is sensitive to at least one of alpha, beta, and gamma particles. In one embodiment, the jacket 48 is made of a plastic and has a diameter of, for example, between 170 and 500 μm.

As shown, the optical fibers 14 and 15 are wound into coils. Preferably, the optical fibers have an extremely low bend loss, and the coils thereof have a relatively large number of turns about a substantially small area. For example, the coils of the optical fibers 14 and 15 may have between approximately 20 and 40 turns and have a diameter of approximately 1 centimeter (cm). Generally, the longer the optical path, such as provided by the optical fibers 14 and 15, the greater the signal-to-noise ratio of the sensor 10. To improve the signal-to-noise ratio of the sensor 10, the optical path may be increased by increasing the number of turns of the optical fiber coils. In the optical fibers 14 and 15, light introduced by the recirculator 22 traverses mostly inside the cores, and only about a few percent of the optical energy of light is contained outside the cores of the optical fibers 14 and 15.

In operation, light produced by the light source 16 is directed to the reflectors 18 and 19 which in turn direct this light to the recirculator 22. A first portion of the light is transmitted through the recirculator 22 and into the first end of the first optical fiber 14 and/or the second optical fiber 15 to propagate around the respective coil thereof (e.g., in a clockwise direction). A second portion (i.e., the reflected portion or wave) is reflected from the recirculator 22 to the photo-detectors 24 and 25. The second portion impinging on photo-detector 24 is derived from light directed at the recirculator 22 from mirror 19, and second portion impinging on photo-detector 25 is derived from light directed at recirculator 22 from mirror 18. The resonance frequency for the path through the first optical fiber 14 and/or the second optical fiber 15 is based on a constructive interference of successively circulated beams in each optical path. After the first portion of light propagates through the core of the respective optical fibers, the light emerges from a second end thereof.

In this exemplary embodiment, the light emerging from the second end is directed to the recirculator 22. A portion of this light is reflected back into the first end of the respective optical fiber by the recirculator 22 while another portion is transmitted (i.e., the transmitted portion or wave) by the recirculator 22 to the photo-detectors 24 and 25. The transmitted waves are a fraction of, and derived from, the recirculating light wave inside the resonators 28 and 29. As the frequency of the light is detuned away from the resonance of each resonator, the transmitted portion becomes very small and only the reflected portion impinges on either photo-detector 24 or 25, indicating a maximum intensity with very little destructive interference. As the frequency of the light is scanned through the center of a resonator resonance, the transmitted wave is maximized for that resonator to produce a maximum destructive interference with the reflected wave, and thus providing a resonance dip having a minimum that is indicative of the resonance center.

To observe the resonance center-frequency of either resonator 28 or 29 (or both), in either the first optical fiber 14 or the second optical fiber 15, the intensity at photo-detectors 24 and 25, respectively, may be measured or a standard synchronous detection technique may be used. In the case of synchronous detection, the input light beam is sinusoidally phase-modulated, and therefore frequency modulated at a frequency ($f_m$) to dither the input beam frequency across a resonance lineshape as measured by the photo-detectors 24 and 25. For example, the electronic circuitry 26 may demodulate the output of the photo-detector 24 at $f_m$ to measure the resonance center indicated by the light output of the circulating light beam. At a line center of the resonance lineshape, or the resonance center, the photo-detector 24 detects a minimum output at the fundamental detection frequency $f_m$ and detects a maximum on either side of the lineshape where the slope of the lineshape is greatest.

When the resonator is off-resonance, an intensity signal maximum is observed, but the signal at $f_m$ is substantially zero. To observe the line width of the resonance lineshape, the light source 16 frequency is monotonically scanned such that the light intensity signal on either photo-detector 24 or 25 experiences at least a sequence of observing a half maximum, then the minimum, then another half maximum. Alternatively, a second measure of the lineshape width may be measured by monitoring the frequency difference between maxima of the demodulated signal at $f_m$, as the light source 16 frequency is scanned monotonically. In this case, a measurement of the frequency width of the resonance between points of highest slope is proportional to the resonator line width, and thus proportional to the loss of the resonator. The light source 16 frequency excursion from half-maximum to half maximum (e.g., between points of highest slope) is the resonator line width (e.g., proportional to the resonator line width), which is indicative of the loss within the respective optical fiber (14 or 15) and a measure of the presence of a hazardous material. Widening of the line width represents the presence of such a hazardous material.

In one embodiment, the light source 16 frequency excursion is measured by recording the light source 16 frequency difference between the time that the photo-detectors 24 and 25 observe on half-maximum signal and the time the photo-detectors 24 and 25 observe the second half-maximum signal. The light source 16 frequency at each of those two points in time may be measured directly or indirectly. One example of direct measurement involves beating the light source 16 frequency with another light source that is not being scanned and measuring the beat frequency difference between the two points in time. An example of indirect measurement, which may be less expensive, is to pre-calibrate the light source 16 frequency versus the electrical signal input used to scan the light source 16. When a laser is used for the light source 16, the electrical signal may be a current drive signal that changes the injection current of the laser, a current drive signal to a thermo-electric cooler that changes the temperature of the laser, or a voltage drive signal to a piezoelectric transducer that changes the path length of the laser cavity to change the laser frequency. In these cases, the laser frequency shift versus the drive signal may be factory-calibrated, in which case the drive signal excursion is a measure of frequency excursion during operation.

When $f_0$ is tuned away from the resonance frequency of the resonators 28 or 29, the light that is transmitted by the recirculator 22 does not enter the optical fibers and is reflected off the recirculator 22 to produce a maximum intensity at the photo-detectors 24 and 25, respectively. When $f_0$ is tuned at the resonance frequency of one of the resonators 28 or 29, the light beam enters the optical fiber (14 or 15), and the light striking the one of the photo-detectors 24 or 25 has a minimum output thereby indicating the resonance center.

The behavior of resonators 28 and 29, in particular the lineshape detected by the photo-detectors 24 and 25 respectively for on-resonance propagation through the first or second optical fibers 14 and 15, is altered when the first and/or second optical fibers 14 and 15 is in the presence of the particular hazardous material 54 associated with that optical fiber. That is, when the first optical fiber 14 is in the presence of the particular biological or chemical agent, the biological or chemical agent permeates the cladding 36 and the indicator 42 (FIG. 2) reacts (e.g., binds) with the biological or chemical agent and alters the optical properties of the first optical fiber 30. For example, the altered optical properties of the first optical fiber 30 may include, but are not necessarily limited to, a change in the index of refraction or an increase or decrease in the optical absorbance or fluorescence. When the second optical fiber is in the presence of a particular type of radioactivity, the radiation passes through the jacket 48 and the cladding 46 of the second optical fiber 15 and into the core 44 where it interacts with the dopant 50. The interaction between the radiation and the dopant 50 reduces the transmittance of light passing through the core 44.

Figure 4:
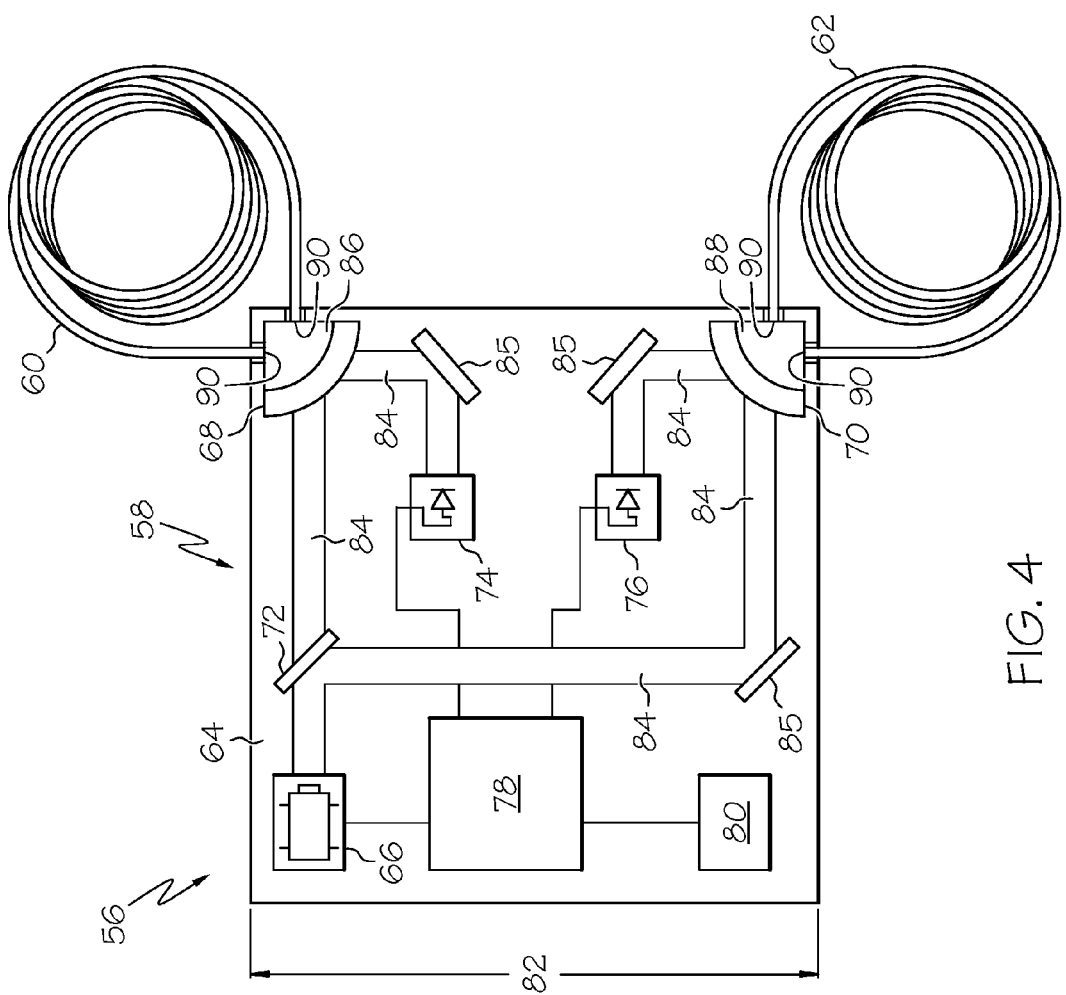
FIG. 4 is a plan view of a hazardous material sensor including a silicon substrate in accordance with another embodiment of the present invention.

FIG. 4 illustrates a fiber optic hazardous material sensor 56 according to an exemplary embodiment. The sensor 56 includes an integrated optical chip (IOC) 58, a first optical fiber 60, and a second optical fiber 62. In the embodiment shown in FIG. 4, the IOC 12 includes a substrate 64 having a light source 66, first and second recirculators 68 and 70, a beam splitter 72, first and second photo-detectors 74 and 76, a controller 78, and a transmitter 80, all of which are formed (or positioned) thereon. Similarly to the embodiment shown in FIG. 1, the hazardous material sensor 56 may be understood to be implemented similarly to a resonator fiber optic gyro (RFOG), as will be appreciated by one skilled in the art.

In the embodiment depicted in FIG. 4, the substrate 64 is substantially rectangular (e.g., square) with a side length 82 of, for example, less than 3 centimeters (cm), such as between 5 millimeters (mm) and 1.5 cm, and a thickness of, for example, between approximately 600 and 100 micrometers (μm). In one embodiment, the substrate 64 is made of silicon, while in another it is indium-phosphide (InP). It should be appreciated that these dimensions, shape, and materials are merely exemplary, and that the substrate 64 could be implemented according to any one of numerous dimensions, shapes, and materials.

The light source 66, at least in the depicted embodiment, is positioned near a corner of the substrate 64 and oriented, or "aimed," at another corner of the substrate 64 and/or the first recirculator 68. In one embodiment, the light source 66 is a laser diode formed or mounted onto the substrate 64. As will be appreciated by one skilled in the art, the laser diode may be formed by doping a very thin layer on the surface of a doped crystal wafer to form a p-n junction, or diode, having an "n-type" region and a "p-type region." Although not specifically illustrated, the light source 66 may be an external cavity laser diode and may include a cavity-length modulation mechanism to tune and/or adjust the frequencies of the laser light emitted therefrom, as is commonly understood. Additionally, elements may be included with the light source 66 that are mounted or formed external to the laser cavity to shape or collimate or optically isolate the laser beam, such as one or more lenses and an optical isolator.

In the embodiment shown in FIG. 1, the first recirculator 68 is positioned near the corner of the substrate 64 at which the light source 66 is aimed, and the second recirculator 70 is positioned near a corner of the substrate 64 opposing the light source 66. In one embodiment, the recirculators 68 and 70 are concave mirrors with a very high reflectivity (e.g., above 95%) and a non-zero transmittance. As is commonly understood, the first and second recirculators 68 and 70 may have a reflectivity for a desired state of polarization of light that is significantly higher than the reflectivity for the state of polarization of light that is orthogonal to the desired state of polarization of light. The recirculators 68 and 70 are shaped to focus light propagating from the light source 66 into the respective first and second optical fibers 60 and 62 and to reflect and focus light propagating from each end of the optical fibers 60 and 62 towards and into the opposing ends of the optical fibers 60 and 62. The partial transmittance of the recirculators 68 and 70 allows a portion of the light from the light source 66 into the optical fibers 60 and 62 and a portion of the light circulating in the optical fibers 60 and 62 to be transmitted therethrough.

Still referring to FIG. 1, the beam splitter 72 is positioned near a side of the substrate 64 between the light source 66 and the first recirculator 68. Although not illustrated in detail, the beam splitter 72 is preferably oriented at an angle (e.g., 45 degrees) relative to a line interconnecting the light sources 66 and the first recirculator 68.

The first and second photo-detectors 74 and 76 are positioned on the substrate 64 near a central portion thereof. In a preferred embodiment, the first and second photo-detectors 74 and 76 each include a photodiode having, for instance a germanium-doped region formed on the substrate 64 if the substrate is silicon and the wavelength is in the infra-red (IR) region. If the substrate is silicon and an optical wavelength is used, the detectors may be silicon photo-diodes formed directly in the substrate, as they could be an indium gallium arsenide phosphide (InGaAsP) photodiode for an InP substrate if the optical wavelength is in a suitable IR wavelength range. In another embodiment, the photo-detectors 74 and 76 include discrete photo-detector chips made of, for example, germanium, silicon, or InGaAsP.

The controller 78 (or processing subsystem), in one embodiment, is formed on or within the substrate 64, and as will be appreciated by one skilled in the art, may include electronic components, including various circuitry and/or integrated circuits (e.g., a microprocessor and a power supply), such as an Application Specific Integrated Circuit (ASIC) and/or instructions stored on a computer readable medium to be carried out by the microprocessor to perform the methods and processes described below. As shown, the controller 78 is in operable communication with and/or electrically connected to the light source 66, the first and second photo-detectors 74 and 76, and the transmitter 80. The transmitter 80 is formed on the substrate 64 and includes, for example, a radio frequency (RF) transmitter, as is commonly understood.

Still referring to FIG. 1, the IOC 58 and/or the substrate 64, in one embodiment, is a "silicon optical bench," as is commonly understood, and may include a series of trenches (or waveguides) 84 and reflectors 85 formed within (or positioned on) the substrate 64. The trenches 84 provide clearance, and the reflectors 85 optically interconnect the light source 66, the beam splitter 72, the first and second photo-detectors 74 and 76, and the first and second recirculators 68 and 70. In the depicted embodiment, the substrate 64 also includes first and second recirculator cavities 86 and 88 formed adjacent to the concave (i.e., outer) side of the respective first and second recirculators 68 and 70 and two v-grooves 90 formed in an outer walls of the recirculator cavities 86 and 88 near the respective corners of the substrate 64.

The first and second optical fibers 60 and 62 have first and second opposing ends inserted into the v-grooves 90 adjacent to the respective recirculator cavities 86 and 88, and in one embodiment, are wound into coils of a diameter of, for example, between 15 and 125 mm. The first and second optical fibers 60 and 62 may otherwise be similar to the respective optical fibers 14 and 15 illustrated in FIGS. 2 and 3 and described above, and may likewise form respective resonators with the first and second recirculators 68 and 70. Although not shown, the optical fibers 60 and 62 may be housed in a permeable or semi-open package.

The various optical components on the substrate 64, such as the recirculators 68 and 70 and the reflectors 85, may have feature sizes of as little as 10 microns, and such may eliminate large bulk optics, even though light from the light source 66 may be traveling in free space. By etching, forming, or placing the optical components and the controller on the substrate, a substantially small, low cost silicon optical gyro may be manufactured that is ideal for high volume production. Although the substrate and material system is preferably silicon, other materials (e.g., alumina, nitrides, III-V elements, other refractory materials, and the like) having suitable properties may be utilized for the substrate.

Still referring to FIG. 4, in operation, the light source 66 emits laser light towards the beam splitter 72 where it is split into first and second portions. The first portion propagates towards, and at least partially through, the first recirculator 68. The second portion is directed towards the opposing side of the substrate 64 and then reflected towards, and at least partially through, the second recirculator 70. At least some of the first and second portions of light enter the first end the respective first and second optical fibers 60 and 62 (when the laser frequency is tuned near resonance of the resonator formed by fiber 60 and recirculator 68 or the resonator formed by fiber 62 and recirculator 70), propagates around the respective coils, and is emitted out of the second of the respective optical fibers back towards the recirculators 68 and 70. Some of the light is transmitted through the recirculators 68 and 70 and reflected into the first and second photo-detectors 74 and 76.

The controller 78 tunes the light source 66 in order to separately determine the resonance frequencies of the resonators associated with each of the first and second optical fibers 60 and 62 in a manner similar to that described above. The controller then toggles between the resonance frequencies while monitoring the resonance line shape detected by the first and second photo-detectors 74 and 76. While the light source 66 is tuned to the resonance frequency of the resonator associated with the first optical fiber 60, a change in the line shape (similar to that described above) detected by the first photo-detector 74 indicates that the first optical fiber 60 has been exposed to the particular biological or chemical agent associated with the first optical fiber 60. Likewise, while the light source 66 is tuned to the resonance frequency of the resonator associated with the second optical fiber 62, a chance in the line shape detected by the second photo-detector 76 indicates that the second optical fiber 62 has been exposed to the type of radiation associated with the second optical fiber 62.

Figure 5:
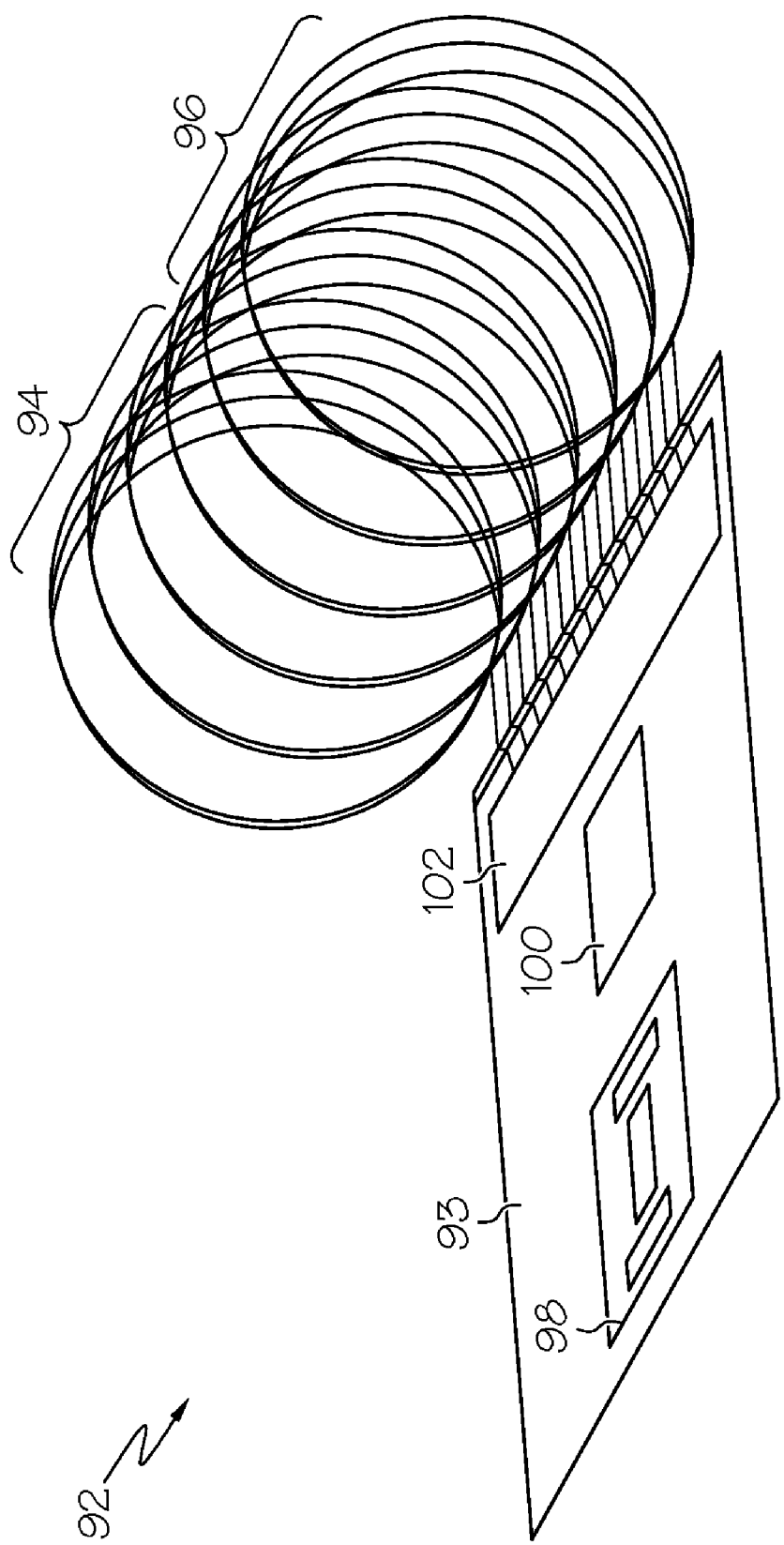
FIG. 5 is an isometric view of a hazardous material sensor including a multiplexer in accordance with a further embodiment of the present invention.

FIG. 5 illustrates a fiber optic hazardous material sensor 92 according to a further embodiment of the present invention. The sensor 92 comprises an IOC 93 and first and second sets 94 and 96 of optical fibers coupled to the IOC 93. Although not illustrated in detail, the IOC 93 includes a light source 98, a photo-detector 100, and a multiplexer 102. Although not shown in detail in FIG. 5, the IOC 93 integrates electronics, such as the controller 78 shown in FIG. 4, and optics, such as the beam splitter 72, the reflectors 85, and the photo-detectors 74 and 76 shown in FIG. 4, onto a single substrate similar to the IOC 58 shown in FIG. 4.

In a manner similar to that described above, each of the optical fibers in the first set 94 of optical fibers is configured to facilitate in the detection of a particular biological or chemical agent, and each of the optical fibers in the second set 96 of optical fibers is configured to facilitate in the detection of a particular radiation type. As such, each of the optical fibers in the first and second sets 94 and 96 of optical fibers includes either a chemical indicator 42 or a radiation sensitive dopant 50 (FIGS. 2 and 3) embedded therein.

The multiplexer 102 is formed on the IOC 93 (or a substrate of the IOC 93) and is coupled (e.g., via one or more v-grooves and/or reflectors) to each of the optical fibers in the first and second sets 94 and 96 of optical fibers. The multiplexer 102 directs input light beams to each of the optical fibers and receives output light beams from the optical fibers after circulating therethrough. The output light beams are each directed to the photo-detector 100 from which a resonance lineshape may be determined. The input light beams are each scanned across the resonance frequency of the corresponding optical fiber. As previously mentioned, this may be accomplished using a fixed average input light frequency and scanning the length of each of the resonator path lengths, thus scanning through the resonance lineshape.

As previously discussed, a change in the resonance lineshape width associated with the light output of a particular optical fiber indicates the presence of the corresponding biological or chemical agent or radiation type. The use of the multiplexer 102 allows the light from the light source 98 to be selectively directed to one or more of the optical fibers at any given time.

One advantage of the sensor described above is that the combination of the different substances embedded within the optical fibers allows a single sensor to be used to detect both biological or chemical agents and radioactivity. Another advantage is that because the circuitry and the optical components are formed on a single substrate, in which conventional semiconductor processing techniques may be used, a small and relatively inexpensive hazardous material sensor is provided.

Figure 6:
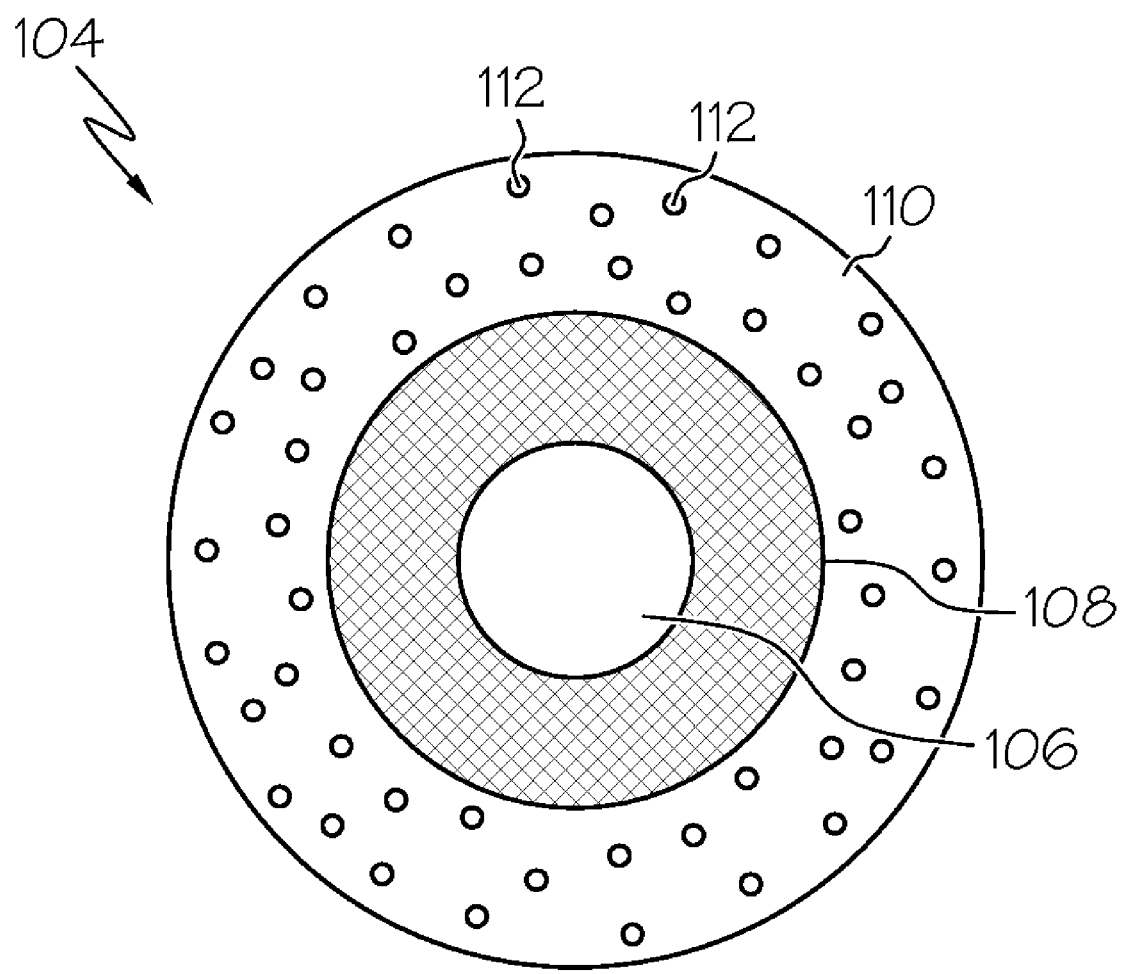
FIG. 6 is a cross-sectional view of an optical fiber for use in a hazardous material sensor in accordance with a further embodiment of the present invention.

FIG. 6 illustrates a cross-section of an optical fiber 104 according to another embodiment of the present invention. The optical fiber 104 includes a core 106, a cladding 108, and an outer jacket 110. Similar to the optical fibers described above, the core 106 may be made of silica glass. The cladding 108 may be formed from silica glass including a photonic crystalline structure. The outer jacket 110, similarly to the cladding 36 shown in FIG. 2, may be made of a permeable polymer-based material and include a biological or chemical indicator 112 embedded therein. As such, the optical fiber 104 may also be suitable for the detection of the particular biological or chemical agent to which the indicator 112 is reactive.

Figure 7:
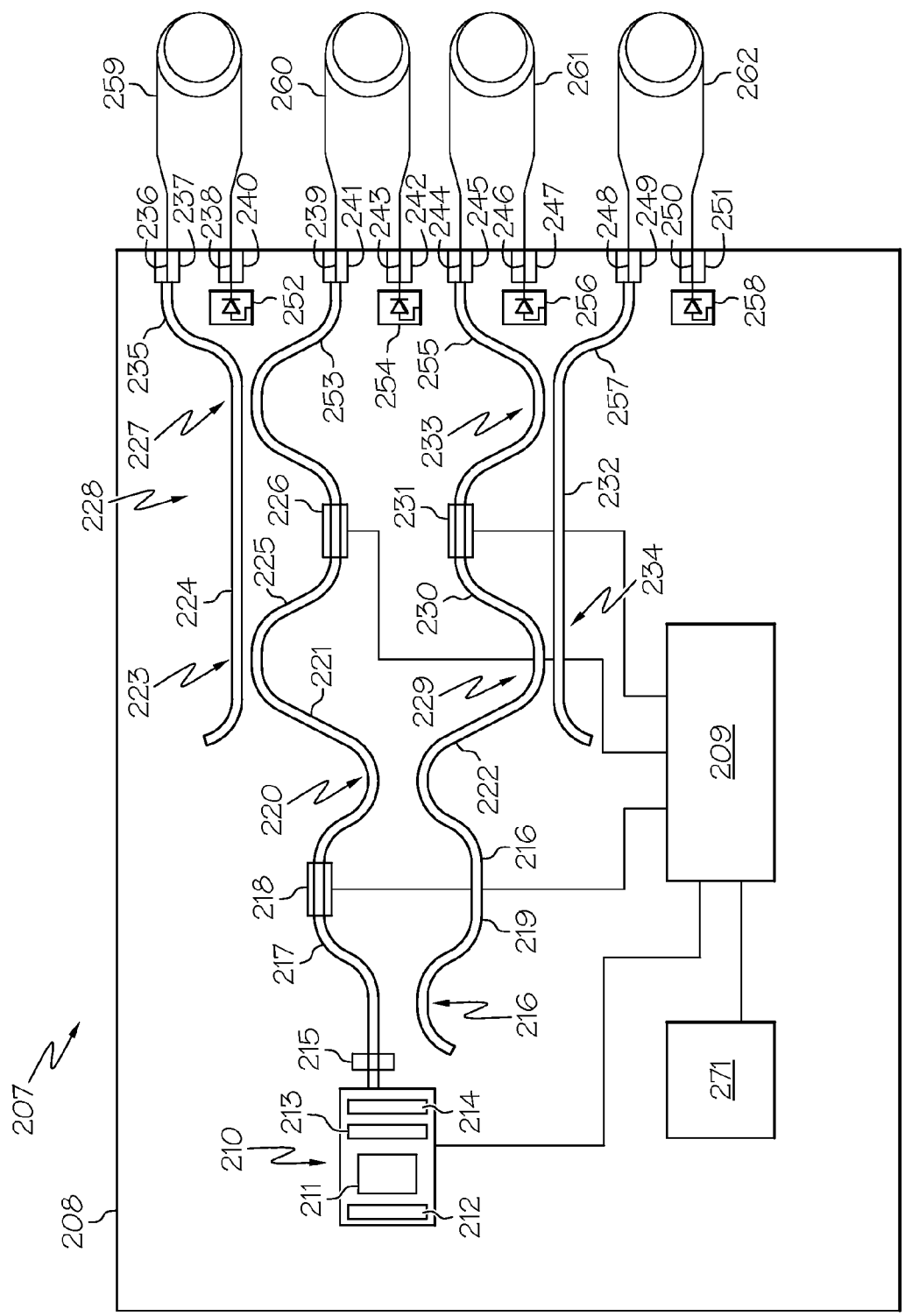
FIG. 7 is a plan view of a hazardous material sensor in accordance with another exemplary embodiment of the present invention.

FIG. 7 illustrates a fiber optic hazardous material sensor 207 according to a further embodiment of the present invention. The sensor 207 includes a substrate 208 and optical fiber coils (e.g., four optical fiber coils). The depicted embodiment includes a first fiber coil 259, a second fiber coil 260, a third fiber coil 261, and fourth fiber coil 262. Included inside or on top of the substrate 208 is a laser assembly 210, a coupling device 215, three optical switches (e.g., Mach-Zehnder Interferometer switches) 228, four photo-detectors 252, 254, 256, and 258, and eight v-grooves 237, 240, 241, 243, 245, 247, 249, and 251, and waveguide segments 221, 222, 235, 253, 255 and 257. Also included within or on top of the substrate is an electronics processor 209 and a communication device (e.g., a transmitter) 271.

The laser 210 is a single frequency laser including a laser diode 211, reflectors and wavelength selective devices 212 and 213, and an external beam shaping and optical isolation element 214. The first Mach-Zehnder Interferometer switch 228 that immediately receives light from the laser includes waveguides 217 and 219 and a modulator 218. Waveguides 217 and 219 are brought into close proximity in two regions to form optical splitter 216 and optical combiner 220. The second Mach-Zehnder Interferometer switch 228 that receives light from waveguide segment 221 includes waveguides 224 and 225 and a modulator 226. Waveguides 224 and 225 are brought into close proximity in two regions to form optical splitter 223 and optical combiner 227. The third Mach-Zehnder Interferometer switch 228 that immediately receives light from waveguide 222 includes waveguides 230 and 232 and modulator 231. Waveguides 230 and 232 are brought into close proximity in two regions to form optical splitter 229 and optical combiner 233. The first fiber coil 259 has fiber ends 236 and 238, each of which has a highly reflective, but partially transmitting surface (not shown) formed on its tip to form a linear resonator within fiber. In a similar manner, three more resonators are formed within the second fiber coil 260, the third fiber coil 261, and the fourth fiber coil 262, respectively.

During the operation of the sensor 207, light from the laser assembly 210 is directed to the coupling device 215, which may be, for example, a combination of a mirror and a prism, that refracts the laser beam into waveguide 217. The light is then split into two substantially equal waves within splitting region 216 before propagating through waveguides 217 and 219. The light in 217 is phase-shifted via a signal from the processor 209 prior to being recombined in combiner 220. The phase shift imparted to the light in modulator (or phase shifter) 218 is controlled to control the ratio of light directed to waveguide 221 or 222, thus effecting an optical switch in the first Mach-Zehnder Interferometer switch. Similarly, light is switched between waveguides 235 and 253, and between waveguides 255 and 257 in the second and third Mach-Zehnder Interferometer switches, respectively.

In one embodiment, light is switched to one resonator at a time. For instance, light from laser 210 is coupled into waveguide 217 via coupling device 215, and may be directed, via a suitable voltage signal to modulator 218, to waveguide 221 that is directed to waveguide 253 (for example), via a suitable signal on phase shifter 226. Light exiting waveguide 253 is then directed to the second resonator from waveguide 253 such that it propagates back and forth within fiber 260 as the laser frequency is tuned to the resonance of the second resonator. A portion of the light propagating within the second resonator is directed to photo-detector 254 via a partially transmitting coating on the fiber tip of fiber end 242. Fiber ends 236, 238, 239, 242, 244, 246, 248 and 250 are placed in fiber v-grooves 237, 240, 241, 243, 245, 247, 249, and 251, respectively, to align the optical fibers to the waveguides for efficient coupling of light.

In a manner similar to that described in FIG. 1, the resonance lineshapes of the various resonators, indicative of a biological or chemical or radiological sources are determined by scanning the laser frequency. The resonator to be monitored is determined by the processor, which directs the light via the switches and selects which resonator to interrogate. An output indicative of the results is conveyed to the user via the processor and communication electronics, the processor being in communication with the photo-detectors. Phase shifters 218 226, and 231 may be thermo-optics devices in the case of silicon, which change the local temperature of a waveguide to change the optical phase shift, or in the case in an electro-optically active substrate material, may be and electro-optic modulator that changes the phase of the light in the waveguide by applying an electric field across the waveguide.

Figure 8:
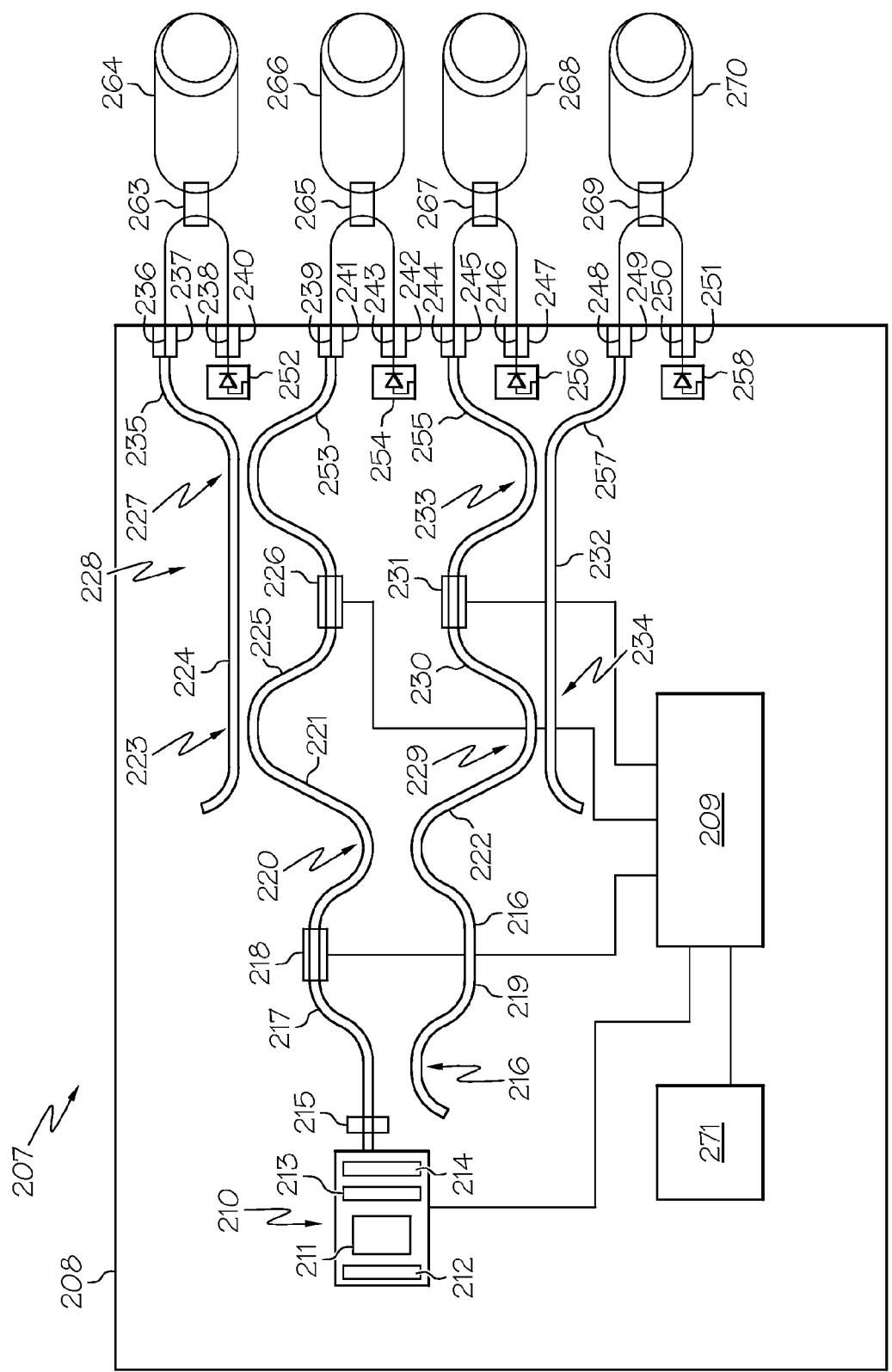
FIG. 8 is a plan view of a hazardous material sensor in accordance with a further embodiment of the present invention.

As will be appreciated by one skilled in the art, various modifications may be made to the sensor 207 shown in FIG. 7. For example, in the sensor 207 shown in FIG. 8, the resonators are formed with recirculators and additional optical fibers forming coils. That is, as shown in FIG. 8, a first recirculator (e.g., fiber coupler) 263 forms a first resonator with a first fiber coil 264, a second recirculator 265 forms a second resonator with a second fiber coil 266, a third recirculator 267 forms a third resonator with a third fiber coil 268, and a fourth recirculator 269 forms a fourth resonator with a fourth fiber coil 270.

Figure 9:
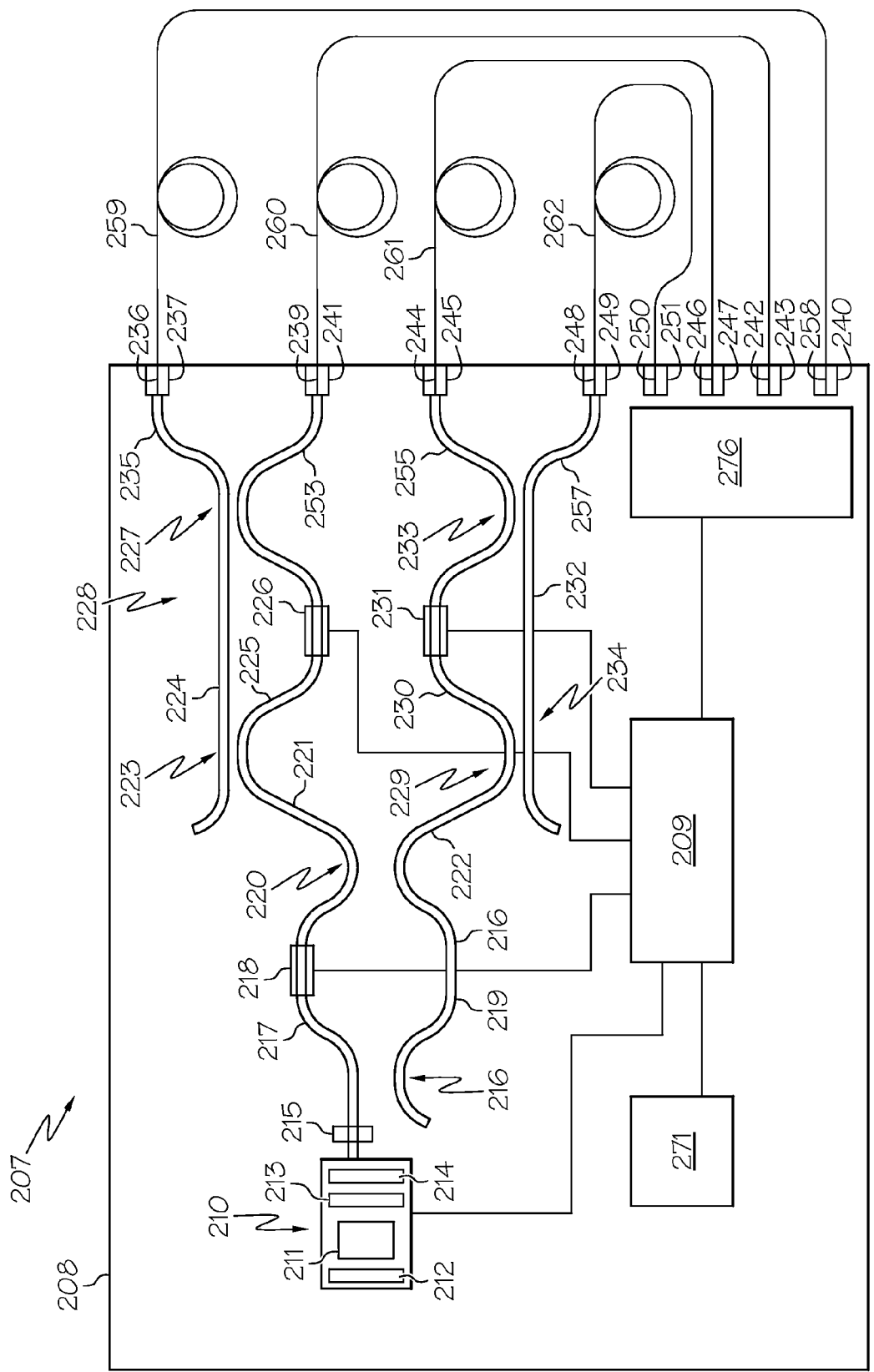
FIG. 9 is a plan view of a hazardous material sensor in accordance with yet a further exemplary embodiment of the present invention.
Figure 10:
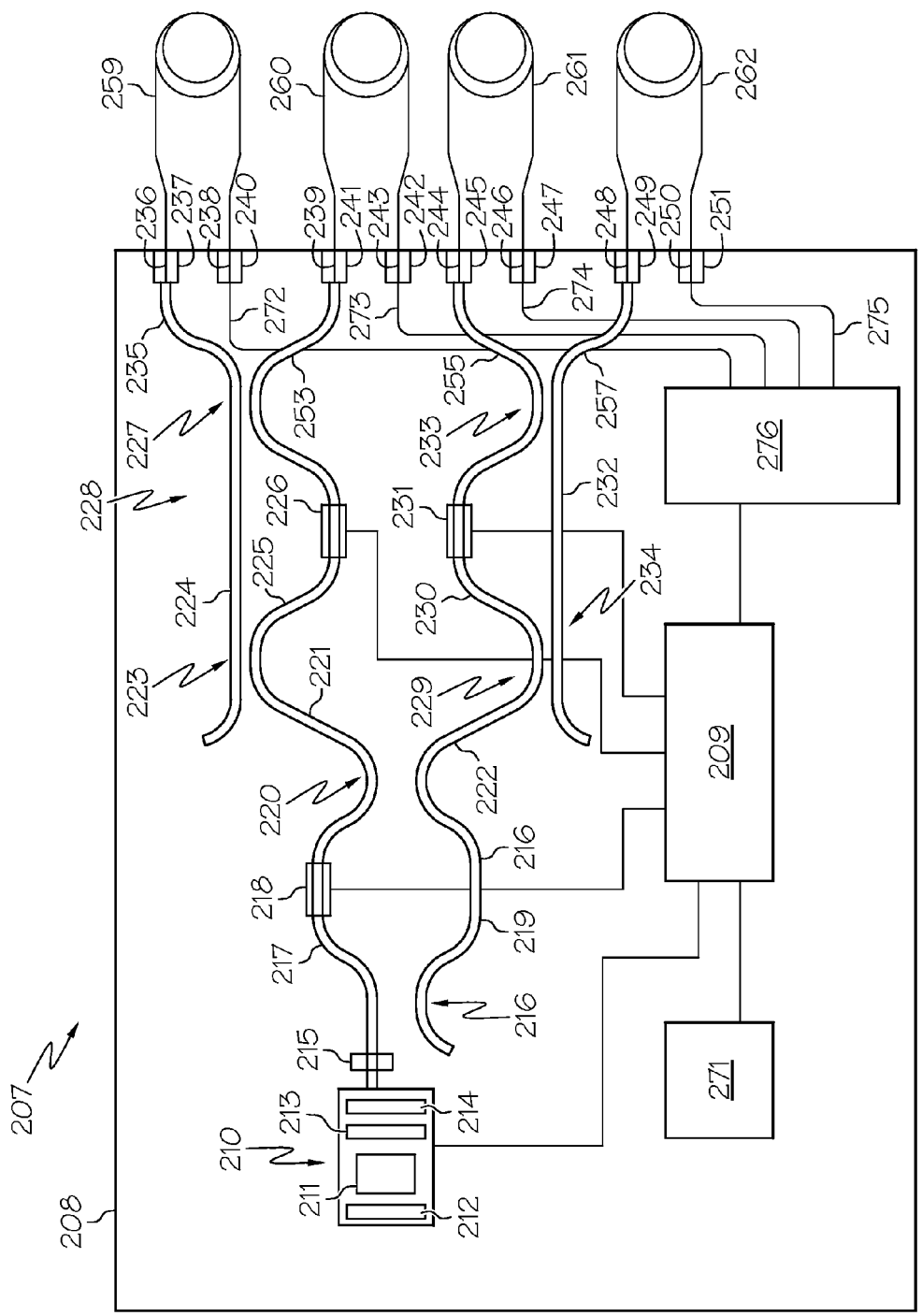
FIG. 10 is a plan view of a hazardous material sensor in accordance with yet a further exemplary embodiment of the present invention.

In the example shown in FIG. 9, v-grooves 240, 243, 245, and 249 are positioned such that the ends 238, 242, 246, and 250 are aligned with a single, relatively large photo-detector 276. An additional advantage of the embodiment shown in FIG. 9 is that because only one photo-detector is utilized, the sensor 207 is somewhat simplified, thus reducing overall costs. In such an embodiment, it may be beneficial to operate the Mach-Zehnder Interferometer switches such that light propagates through only one of the fiber coils at a time. The example shown in FIG. 10 may be similar to that shown in FIG. 9. However, the v-grooves 240, 243, 245, and 249 are positioned as they are in the embodiment shown in FIG. 7 and additional waveguides 272, 273, 274, and 275 are provided to carry the light from the fiber coils to the single photo-detector 276.

It should be noted that although the majority of the discussion herein focuses on the detection of hazardous biological, chemical, and radioactive materials, it will be appreciated by one skilled in the art that the apparatuses and methods described herein may be used for the detection of both hazardous and non-hazardous materials.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. An apparatus for sensing hazardous materials comprising:
    a substrate;
    a first optical fiber coupled to the substrate and having first and second opposing ends and a first substance embedded therein, the first substance being reactive to a first hazardous material type;
    a second optical fiber coupled to the substrate and having first and second opposing ends and a second substance embedded therein, the second substance being reactive to a second hazardous material type that is different from the first hazardous material type; and
    at least one recirculator coupled to the substrate and configured such that when light propagates from one of the ends of at least one of the first and second optical fibers, at least some of the light is directed by the at least one recirculator into the opposing end of the respective optical fiber.

2. The apparatus of claim 1, wherein the at least one recirculator and the at least one of the first and second optical fibers jointly form a resonator having a resonance frequency, the resonator having a first round-trip loss value during an absence of the respective hazardous material type and a second round-trip loss value during a presence of the respective hazardous material type.

3. The apparatus of claim 2, wherein the first hazardous material type includes biological and chemical agents and the second hazardous material type includes radioactivity types.

4. The apparatus of claim 3, wherein each of the first and second optical fibers comprise an inner portion and an outer portion.

5. The apparatus of claim 4, wherein the first substance is embedded within the outer portion of the first optical fiber and the second substance is embedded within the inner portion of the second optical fiber.

6. The apparatus of claim 5, wherein at least some of the light that propagates from the at least one of the first and second optical fibers is transmitted by the at least one recirculator, and further comprising:
    a photo-detector to capture the at least some of the light transmitted by the at least one recirculator;
    a tunable light source operable to emit light towards the at least one recirculator, the recirculator being configured such that at least a portion of the light is transmitted by the recirculator into the at least one of the first and second optical fibers; and
    a processor in operable communication with the photo-detector and the tunable light source and configured to tune the tunable light source through the resonance of the resonator and detect a change from the first round-trip loss value to the second round-trip loss value.

7. The apparatus of claim 6, wherein the processor is further configured to detect a resonance shape centered on the resonance frequency, a change in the resonance shape being indicative of said change from the first round-trip loss value to the second round-trip loss value.

8. The apparatus of claim 7, wherein the outer portion of each optical fiber comprises a permeable polymer-based material and the inner portion of each optical fiber comprises glass.

9. The apparatus of claim 8, wherein the outer portions of the optical fibers comprise a cladding and the inner portions of the optical fibers comprise a core, the claddings being formed around the respective cores.

10. The apparatus of claim 8, further comprising:
    a third optical fiber having first and second opposing ends and a third substance embedded therein, the third substance being reactive to the first hazardous material type; and
    a fourth optical fiber having first and second opposing ends and a fourth substance embedded therein, the fourth substance being reactive to the second hazardous material type;
    wherein the at least one recirculator is further configured such that when light propagates from one of the ends of at least one of the first, second, third, and fourth optical fibers, at least some of the light is directed by the at least one recirculator into the opposing end of the respective optical fiber.

11. A fiber optic hazardous material sensor comprising:
    a substrate;
    a tunable light source on the substrate and operable to emit light;
    a first plurality of optical fibers coupled to the substrate, each having first and second opposing ends and a respective first substance therein, the first substances each being reactive to a first hazardous material type including biological or chemical agents;

a second plurality of optical fibers coupled to the substrate, each having first and second opposing ends and a respective second substance therein, the second substances each being reactive to a second hazardous material type including radioactivity types;

at least one recirculator on the substrate and configured such that a portion of the light emitted by the tunable light source is transmitted therethrough and when light propagates from one of the ends of at least one of the optical fibers, at least some of the light is directed by the at least one recirculator into the opposing end of the respective optical fiber; and a multiplexer on the substrate and coupled between the tunable light source and the first and second plurality of optical fibers, the multiplexer being configured to selectively direct the light from the tunable light source to at least one of the optical fibers of the first and second pluralities of optical fibers, the at least one recirculator and the at least one of the optical fibers jointly forming a resonator having a resonance frequency.

12. The fiber optic hazardous material sensor of claim 11, wherein the multiplexer comprises a plurality of optical switches.

13. The fiber optic hazardous material sensor of claim 12, wherein the plurality of optical switches comprise at least one Mach-Zehnder Interferometer switch.

14. The fiber optic hazardous material sensor of claim 13, wherein the resonator has a first round-trip loss value when light is propagated therethrough during an absence of the respective hazardous material type and a second round-trip loss value when light is propagated therethrough during a presence of the respective hazardous material type.

15. The fiber optic hazardous material sensor of claim 14, wherein at least some of the light that propagates from one of the ends of the at least one of the optical fibers is transmitted by the at least one recirculator, and further comprising:
a photo-detector to capture the at least some of the light transmitted by the at least one recirculator; and
a processor in operable communication with the photo-detector and tunable light source and configured to tune the tunable light source through the resonance of the resonator, detect said change from the first round-trip loss value to the second round-trip loss value, and detect a resonance shape centered on the resonance frequency, a change in the resonance shape being indicative of said change from the first round-trip loss value to the second round-trip loss value.

16. A method for sensing hazardous materials comprising:
generating light with a tunable light source;
arranging at least one recirculator and first and second optical fibers having first and second opposing ends and respective first and second substances embedded therein such that a beam of the light generated with the tunable light source is transmitted by the at least one recirculator, enters the first end of a selected one of the first and second optical fibers, and is emitted from the second end of the selected optical fiber onto the at least one recirculator, a first portion of the beam of light being reflected by the at least one recirculator into the first end of the selected optical fiber and a second portion of the beam of light being transmitted by the at least one recirculator such that the at least one recirculator and the selected one of the first and second optical fibers jointly form a resonator having a resonance frequency, wherein the first substance is reactive to a first hazardous material type including biological or chemical agents and the second substance is reactive to a second hazardous material type including radioactivity types such that the resonator has a first round-trip loss value during an absence of the respective hazardous material type and a second round-trip loss value during a presence of the respective hazardous material type;
capturing the second portion of the beam of light transmitted by the at least one recirculator to determine a present round-trip loss value for the resonator;
tuning the tunable light source through the resonance of the resonator to determine present resonance properties of the resonance line shape; and
monitoring the present resonance properties, a change in the resonance properties being indicative of a change in the round-trip loss value and the presence of the respective hazardous material type.

17. The method of claim 16, further comprising selectively directing the light generated with the tunable light source to only a selected optical fiber of the first and second optical fibers.

18. The method of claim 16, wherein the first and second optical fibers each have inner and outer portions and the first substance is embedded within the outer portion of the first optical fiber and the second substance is embedded within the inner portion of the second optical fiber.

19. The method of claim 18, wherein the outer portion of the first optical fiber comprises a permeable polymer-based material and the inner portion of the second optical fiber comprises glass.

* * * * *